(12) United States Patent
Yokoi

(10) Patent No.: US 8,089,508 B2
(45) Date of Patent: Jan. 3, 2012

(54) CAPSULE TYPE MEDICAL SYSTEM

(75) Inventor: Takeshi Yokoi, Hino (JP)

(73) Assignee: Olympus Corporation, Tokyo (JP)

( * ) Notice: Subject to any disclaimer, the term of this patent is extended or adjusted under 35 U.S.C. 154(b) by 1034 days.

(21) Appl. No.: 11/433,981

(22) Filed: May 15, 2006

(65) Prior Publication Data

US 2006/0209185 A1 Sep. 21, 2006

Related U.S. Application Data

(63) Continuation of application No. pct/jp2004/017009, filed on Nov. 16, 2004.

(30) Foreign Application Priority Data

Nov. 18, 2003 (JP) .................................. 2003-388501

(51) Int. Cl.
*H04N 7/18* (2006.01)
(52) U.S. Cl. ......................................................... 348/64
(58) Field of Classification Search .......................... None
See application file for complete search history.

(56) References Cited

U.S. PATENT DOCUMENTS

| | | | |
|---|---|---|---|
| 5,749,830 A * | 5/1998 | Kaneko et al. ................. | 600/160 |
| 5,871,439 A | 2/1999 | Takahashi et al. | |
| 5,877,819 A * | 3/1999 | Branson ......................... | 348/701 |
| 6,471,636 B1 | 10/2002 | Sano et al. | |
| 6,527,708 B1 | 3/2003 | Nakamura et al. | |
| 7,578,788 B2 * | 8/2009 | Yokoi et al. .................... | 600/160 |

| | | | |
|---|---|---|---|
| 2001/0017649 A1 | 8/2001 | Yaron | |
| 2002/0109774 A1 | 8/2002 | Meron et al. | |
| 2002/0198439 A1 | 12/2002 | Mizuno | |
| 2003/0158503 A1 | 8/2003 | Matsumoto | |
| 2003/0171652 A1 | 9/2003 | Yokoi et al. | |
| 2003/0181788 A1 | 9/2003 | Yokoi et al. | |
| 2003/0213495 A1 | 11/2003 | Fujita et al. | |

FOREIGN PATENT DOCUMENTS

| | | |
|---|---|---|
| EP | 0 655 710 A2 | 5/1995 |
| EP | 1 329 189 A2 | 7/2003 |
| EP | 1 342 447 A2 | 9/2003 |
| JP | 02-031738 | 2/1990 |
| JP | 04-341232 | 11/1992 |
| JP | 09-005643 | 1/1997 |
| JP | 09-066023 | 3/1997 |
| JP | 10-328136 | 12/1998 |

(Continued)

OTHER PUBLICATIONS

Japanese Official Action dated Feb. 23, 2010.

*Primary Examiner* — Nhon Diep
(74) *Attorney, Agent, or Firm* — Scully, Scott, Murphy & Presser, P.C.

(57) ABSTRACT

The present invention provides a capsule type medical system capable of displaying different images on a monitor in such a display mode that a diagnosis can be easily made when one capsule type endoscope includes a plurality of image pickup units. A capsule type endoscope includes a plurality of image pickup elements for generating different image data and a storage unit for previously storing image pickup procedures of the image pickup elements, and records or transmits the different image data, captured in accordance with any of the procedures stored in the storage unit, in time series. An extracorporeal display unit includes a display control section for controlling a method for displaying the different image data recorded or transmitted.

15 Claims, 15 Drawing Sheets

FOREIGN PATENT DOCUMENTS

| | | |
|---|---|---|
| JP | 11-56751 | 3/1999 |
| JP | 11-104059 | 4/1999 |
| JP | 2001-197485 | 7/2001 |
| JP | 2003-38425 | 2/2003 |
| JP | 2003-070728 | 3/2003 |
| JP | 2003-215469 | 7/2003 |
| JP | 2003-275170 | 9/2003 |
| JP | 2003-275171 | 9/2003 |
| JP | 2003-325439 | 11/2003 |
| JP | 2003-325441 | 11/2003 |
| JP | 2004-321603 | 11/2004 |
| JP | 2006-320760 | 11/2006 |
| JP | 4009581 | 11/2007 |
| WO | WO 01/50941 A2 | 7/2001 |
| WO | WO 02/36007 A1 | 5/2002 |
| WO | WO 03/011103 A2 | 2/2003 |

* cited by examiner

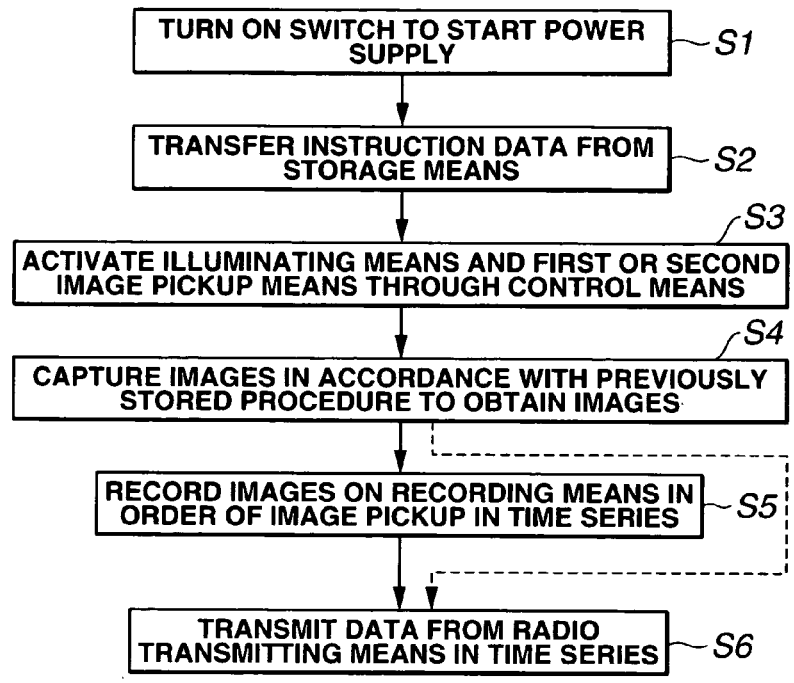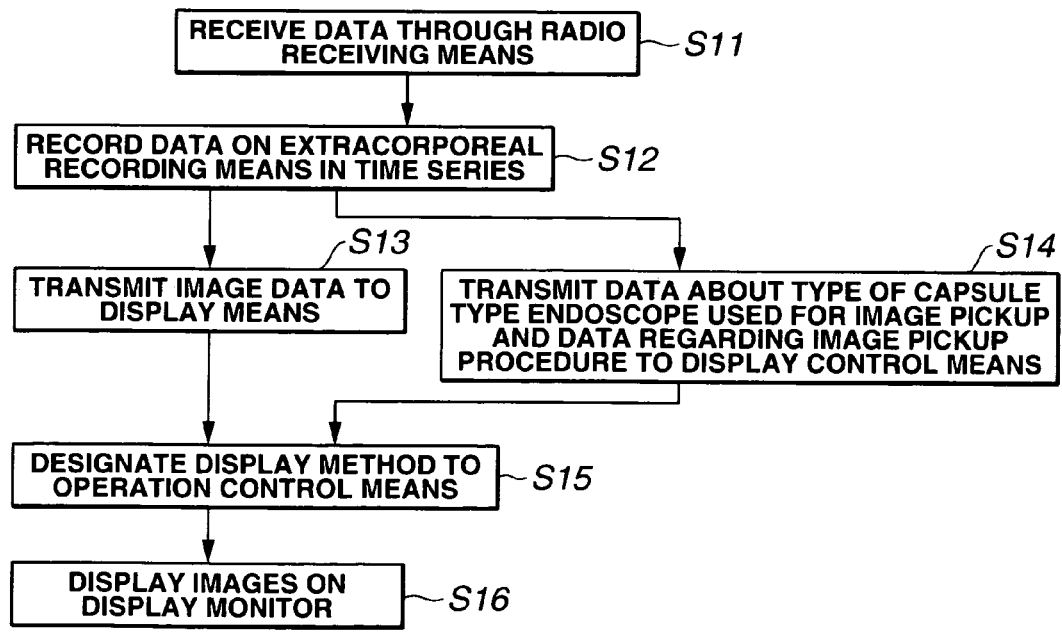

CAPSULE TYPE MEDICAL SYSTEM

CROSS REFERENCE TO RELATED APPLICATION

This application is a continuation application of PCT/JP2004/017009 filed on Nov. 16, 2004 and claims benefit of Japanese Application No. 2003-388501 filed in Japan on Nov. 18, 2003, the entire contents of which are incorporated herein by this reference.

BACKGROUND OF THE INVENTION

1. Field of the Invention

The present invention relates to a capsule type medical system for capturing images in a body cavity using a capsule type endoscope.

2. Description of the Related Art

In recent years, capsule type medical systems for conducting an examination of a body cavity using a capsule type endoscope which is easy to swallow have been proposed.

For example, as a first conventional example, PCT Publication No. WO03/011103A2 discloses a device which is constructed so that first and second images with different depths of focus are focused on an image sensor and which includes at least two light switching units.

As a second conventional example, PCT Publication No. WO02/36007A1 discloses a capsule video for observing a chemically characteristic area.

SUMMARY OF THE INVENTION

The present invention provides a capsule type medical system having at least a capsule type endoscope and an extra-corporeal display unit, the capsule type endoscope including: a plurality of image pickup units for generating different image data; a storage unit for previously storing image pickup procedures of the image pickup units; and a recording/transmitting unit for recording or transmitting at least a part of different image data captured in accordance with any of the procedures stored in the storage unit in time series, the extra-corporeal display unit including: a display control unit for controlling a method for displaying the image data recorded or transmitted.

BRIEF DESCRIPTION OF THE DRAWINGS

FIG. 4A is a flowchart showing the operation based on an operation procedure according to the present embodiment.

FIG. 4B is a flowchart showing the operation based on the operation procedure according to the present embodiment.

DETAILED DESCRIPTION OF THE PREFERRED EMBODIMENT(S)

Embodiments of the present invention will now be described with reference to the drawings.

First Embodiment

Figure 1:
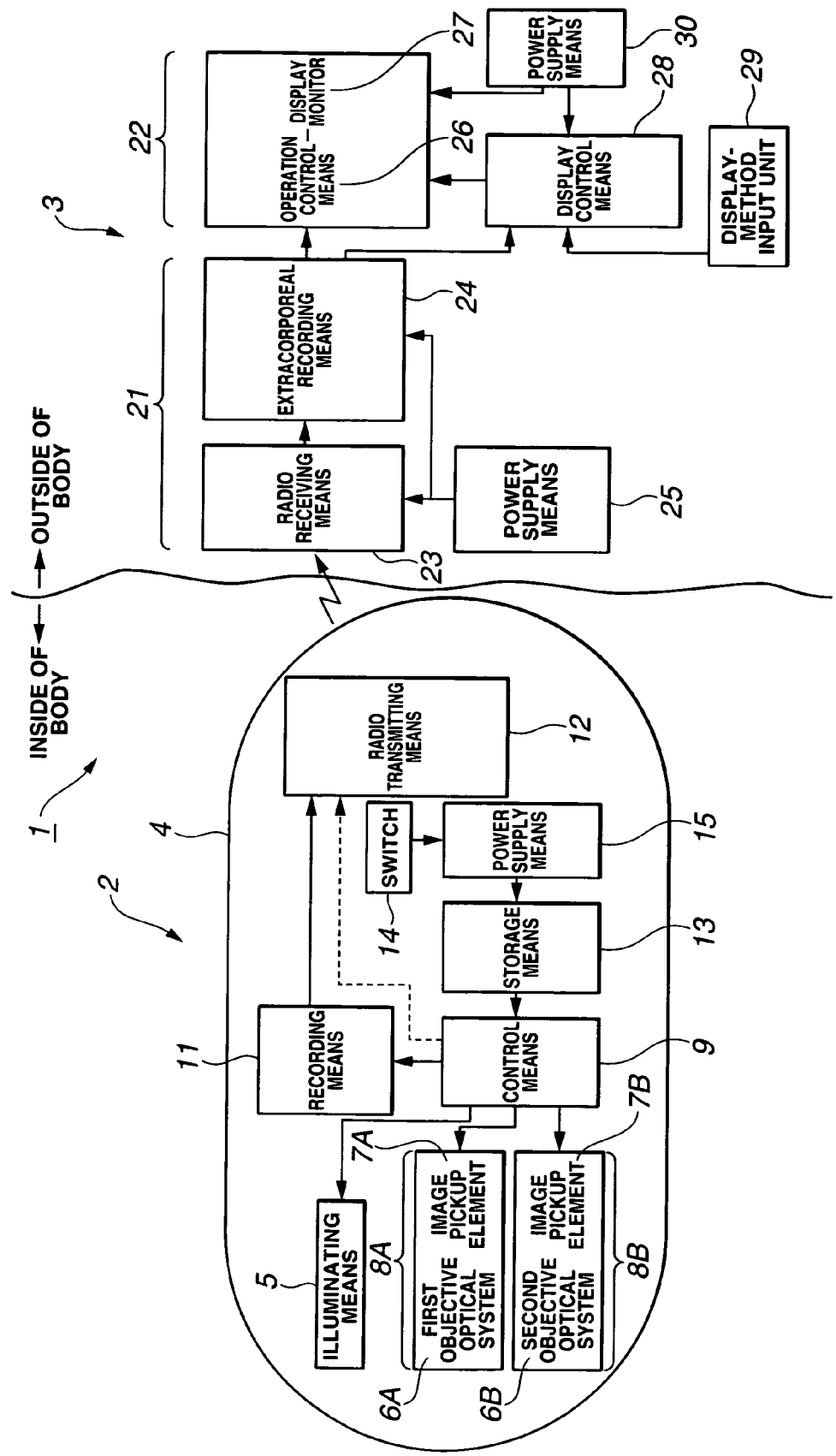
FIG. 1 is a schematic diagram of the structure of a capsule type medical system according to a first embodiment of the present invention.
Figure 2:
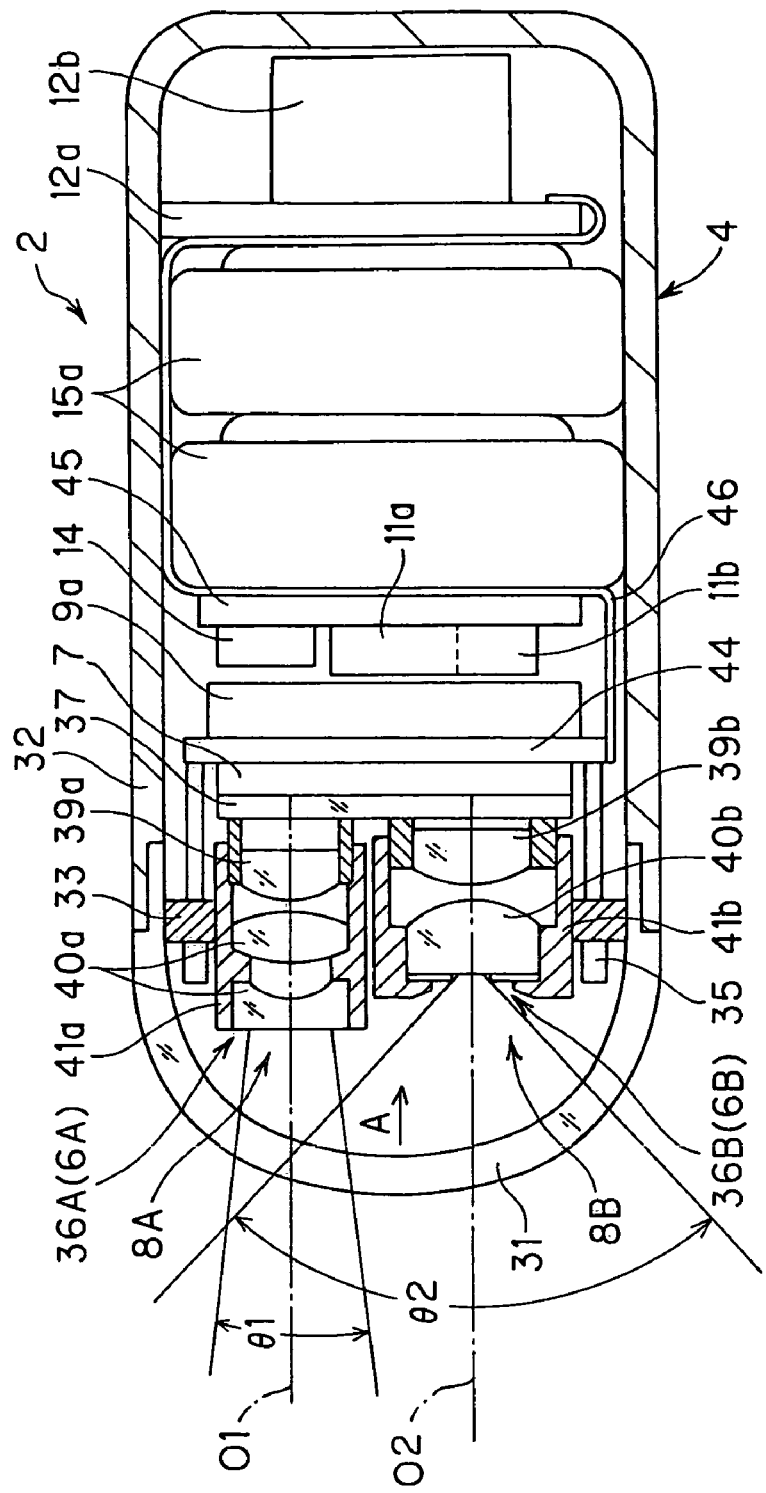
FIG. 2 is a vertical sectional view of the specific structure of a capsule type endoscope according to the first embodiment.
Figure 3:
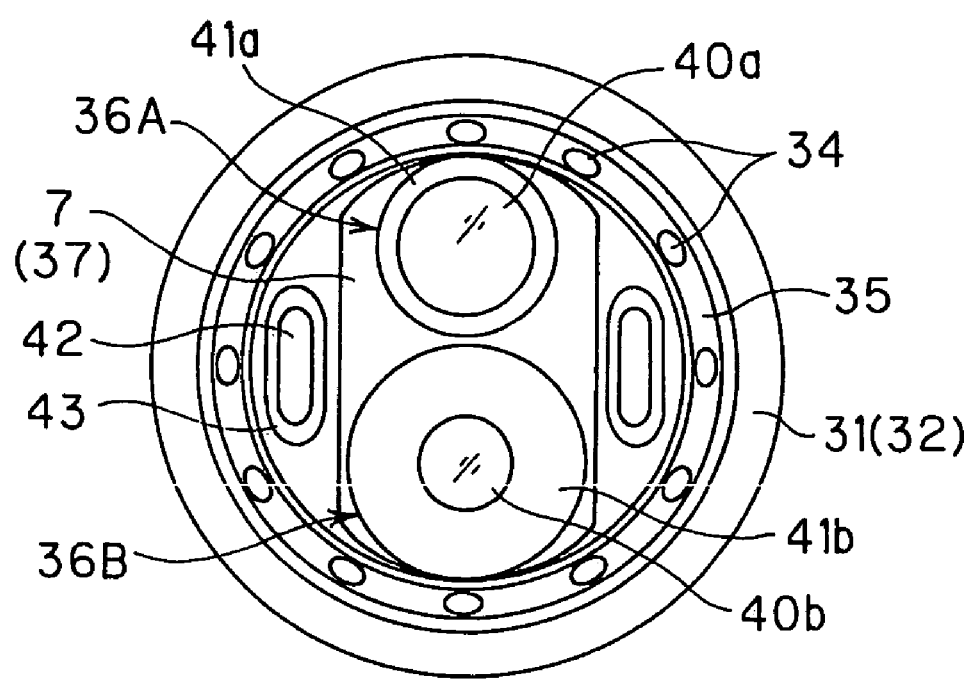
FIG. 3 is a view of the capsule type endoscope, except for a transparent cover in FIG. 2, as viewed in the direction of an arrow A in FIG. 2.
Figure 5:
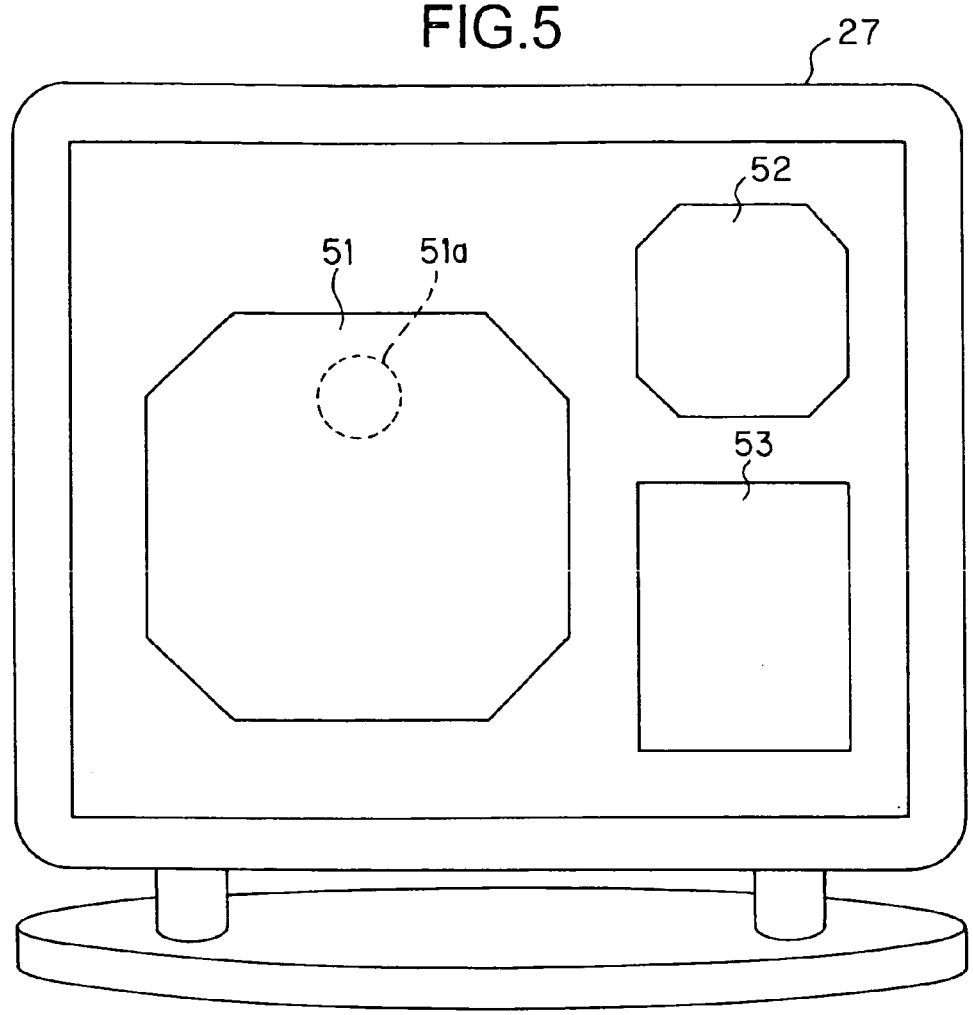
FIG. 5 is a diagram showing a display example in which two kinds of images are simultaneously displayed on a display monitor in accordance with an input operation with respect to a display method.
Figure 7:
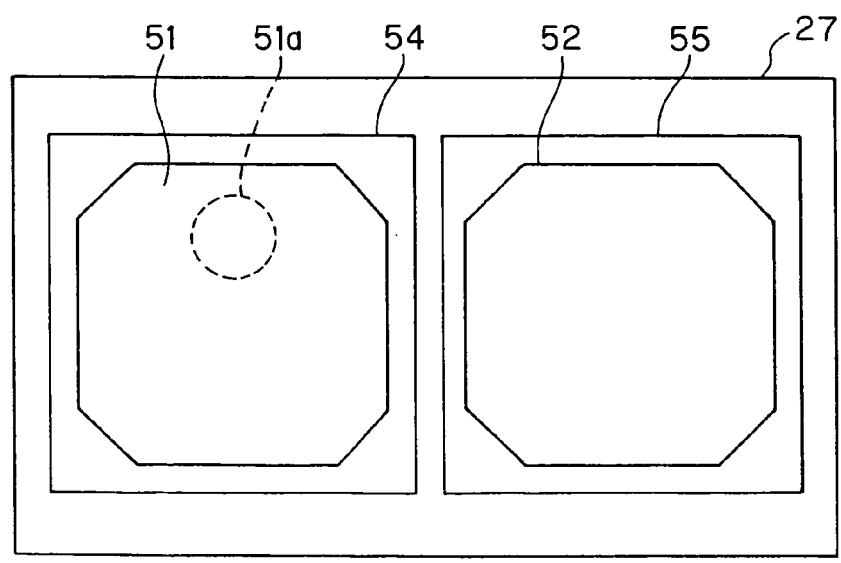
FIG. 7 is a diagram showing another display example on the display monitor.
Figure 6:
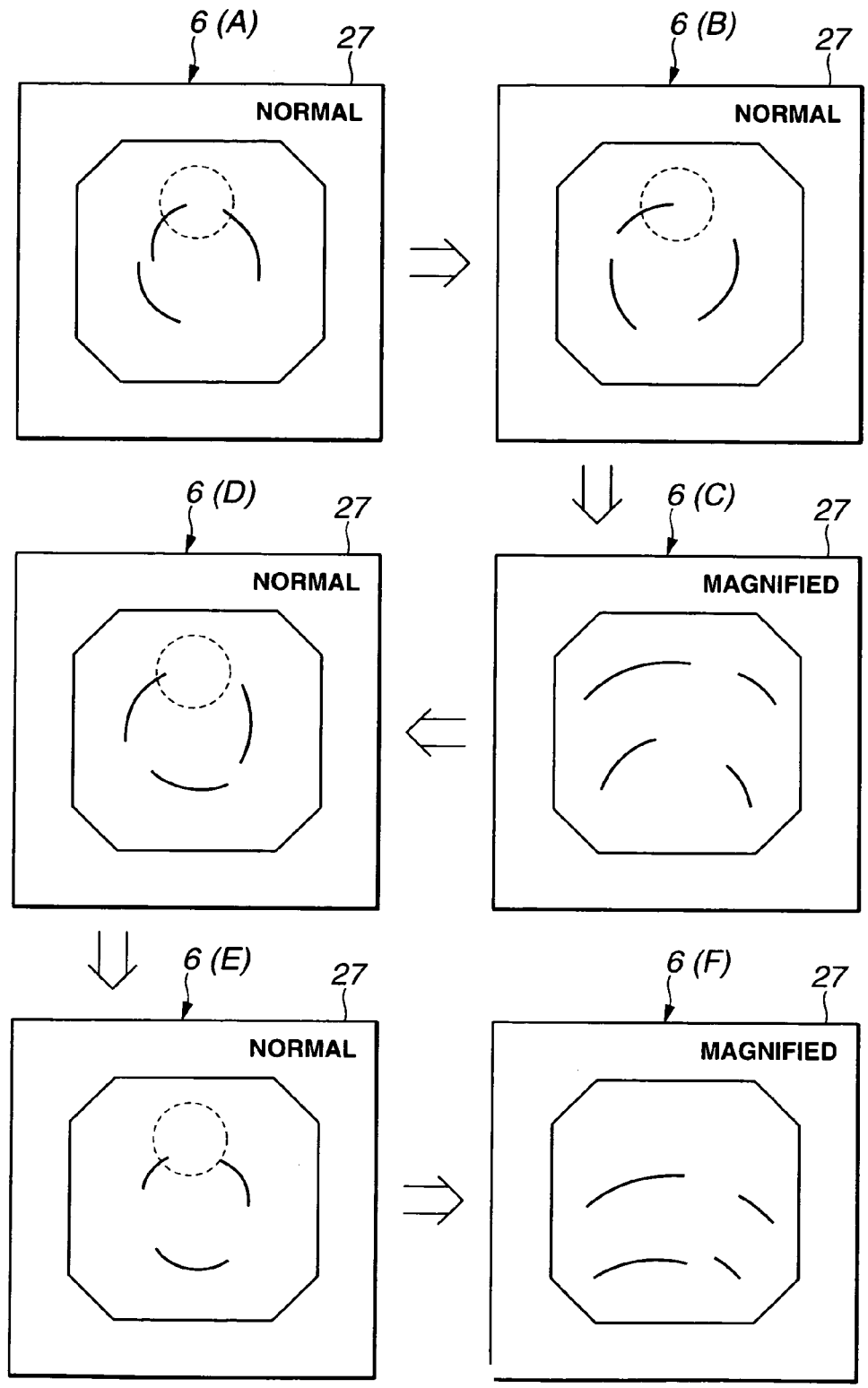
FIG. 6 is a diagram showing another display example in which two kinds of images are sequentially displayed on the display monitor in accordance with an input operation with respect to another display method.

FIGS. 1 to 7 relate to a first embodiment of the present invention. FIG. 1 shows the entire structure of a capsule type medical system according to the first embodiment of the present invention. FIG. 2 is a diagram showing the specific structure of a capsule type endoscope. FIG. 3 is a view of the capsule type endoscope, except for a transparent cover in FIG. 2, as viewed in the direction of an arrow A in FIG. 2. FIGS. 4A and 4B are flowcharts each showing the operation based on an operation procedure according to the present embodiment. FIGS. 5 and 6 show display examples on a display monitor, each example depending on an input operation with respect to a display method. FIG. 7 shows another display example on the display monitor.

As shown in FIG. 1, a capsule type medical system 1 according to the first embodiment of the present invention includes: a capsule type endoscope 2, which is swallowed from a mouth and inserted into a body, for capturing images in vivo; and an extracorporeal device 3, disposed outside the body, for receiving image data transmitted by radio from the capsule type endoscope 2, recording the data in time series, and displaying the data.

The capsule type endoscope 2 includes: illuminating means 5 for illumination; first image pickup means 8A having a first objective optical system 6A and a solid-state image pickup element 7A disposed at the image forming position of the objective optical system 6A; and second image pickup means 8B having a second objective optical system 6B and a solid-state image pickup element 7B placed at the image forming position of the objective optical system 6B, the means 5, 8A, and 8B being arranged in a capsule type housing 4. Instead of the solid-state image pickup elements 7A and 7B, a common solid-state image pickup element 7 may be used as shown in FIG. 2 and the like.

The illuminating means 5 and the first and second image pickup means 8A and 8B are connected to control means 9 for performing signal processing and control. The control means 9 controls illumination and image pickup and performs signal processing on image pickup signals generated by the solid-state image pickup elements 7A and 7B. The control means 9 further compresses image data obtained by A/D conversion and records the data on recording means 11. In addition, the control means 9 transmits the compressed image data recorded on the recording means 11 to radio transmitting means 12. The radio transmitting means 12 high-frequency modulates the image data and transmits the data by radio. In other words, the control means 9 controls the recording means 11 to record captured image data in time series in the order of image pickup and also controls the radio transmitting means 12 to transmit captured image data in time series.

Alternatively, after image data is temporarily recorded on the recording means 11 by the control means 9, the image data read from the recording means 11 may be transmitted to the radio transmitting means 12 and the radio transmitting means 12 may transmit the image data by radio.

Control program data handled by the control means 9 is stored in storage means 13. When power supply means 15 is turned on using a switch 14, the control means 9 reads the control program data in the storage means 13 and controls the operation of the capsule type endoscope 2 in accordance with the control program data.

On the other hand, the extracorporeal device 3 includes a recording unit 21 for receiving image data transmitted from the capsule type endoscope 2 and recording the data, and a display unit 22 for displaying an image through the recording unit 21.

The recording unit 21 includes radio receiving means 23 for receiving image data transmitted via radio waves from the radio transmitting means 12 by radio. The radio receiving means 23 demodulates the received image data and transmits the data to extracorporeal recording means 24. The extracorporeal recording means 24 records the image data. The radio receiving means 23 and the extracorporeal recording means 24 are supplied with operating power from power supply means 25.

Image data recorded on the extracorporeal recording means 24 is sequentially read by operation control means 26 constituting the display unit 22 and is then subjected to display processing. After that, the data is transmitted to a display monitor 27. Images captured by the first and second image pickup means 8A and 8B of the capsule type endoscope 2 are displayed on a display screen of the display monitor 27.

The operation control means 26 and the display monitor 27 are controlled by a display control section (hereinafter, referred to as display control means) 28 serving as display control means. A user inputs an instruction regarding a display method through a display-method input unit 29, so that the user can select and set a method for displaying images through the display control means 28. The display control means 28 can also control a display method set by the display control means 28 on the basis of information previously stored in the storage means 13 of the capsule type endoscope 2. According to the present embodiment, as described above, a method for displaying images obtained through the capsule type endoscope 2 on the display monitor 27 can be changed suitable for diagnosis or in accordance with setting selected by the user.

The operation control means 26, the display monitor 27, and the display control means 28 are supplied with operating power from power supply means 30.

As the storage means 13 in the capsule type endoscope 2, an EEPROM rewritable during manufacturing or a mask ROM that is not rewritable but is inexpensive can be used.

As the recording means 11 in the capsule type endoscope 2, a memory, such as an SRAM, can be used. As the extracorporeal recording means 24, a large-capacity rewritable storage medium, such as a flash memory or a hard disk, can be used.

FIGS. 2 and 3 show the specific structure of the capsule type endoscope 2. A transparent semispherical tip cover 31 is engaged with a cylindrical outer case 32 having a semispherical closed rear end. The cover and the case are fixed to each other by bonding, thus forming the capsule type housing 4 having a watertight structure.

A ring-shaped illumination board 33 is disposed in the tip cover 31. Many light emitting units 34, such as white LEDs, are arranged along the circumference of the illumination board 33, thus forming ring-shaped illuminating means 35 as shown in FIG. 3.

In a region surrounded by the illumination board 33, a magnified-observation objective optical system 36A corresponding to the first objective optical system 6A in FIG. 1 and a normal-observation objective optical system (or a wide-range-observation objective optical system) 36B corresponding to the second objective optical system 6B in FIG. 1 are adjacent to each other, e.g., vertically. Those optical systems 36A and 36B form optical images on, e.g., the common solid-state image pickup element 7 covered with a common cover glass 37, respectively, such that the optical images are spaced vertically. The solid-state image pickup element 7 includes a CCD or a CMOS sensor. As mentioned above, two optical images are formed on the common solid-state image pickup element 7. This arrangement enables the capsule type endoscope to be smaller than a capsule type endoscope including separate solid-state image pickup elements.

The magnified-observation objective optical system 36A includes a fixed lens 39a, which is attached to a lens frame fixed to the cover glass 37, and a movable lens group 40a mounted in a movable lens frame 41a, which is engaged with the above-mentioned lens frame.

The normal-observation objective optical system 36B includes a fixed lens 39b, attached to another lens frame fixed to the cover glass 37, and a movable lens 40b mounted in a movable lens frame 41b, which is engaged with the above-mentioned lens frame.

In the magnified-observation objective optical system 36A, focus adjustment is performed in such a manner that the movable lens group 40a is moved along an optical axis O1 relative to the fixed lens 39a so that an optical image is focused on the light receiving surface of the solid-state image pickup element 7 and, after that, the movable lens frame 41a is fixed to the corresponding lens frame. An observation range θ1 for magnified observation of the magnified-observation objective optical system 36A is substantially in the range of 20° to 50°.

In the normal-observation objective optical system 36B, focus adjustment is performed in such a manner that the movable lens 40b is moved along an optical axis O2 relative to the fixed lens 39b so that an optical image is focused on the light receiving surface of the solid-state image pickup element 7 and, after that, the movable lens frame 41b is fixed to the corresponding lens frame. An observation range θ2 of the normal-observation objective optical system 36B is approximately in the range of 90° to 140°.

As described above, according to the present embodiment, the magnified-observation objective optical system 36A and the normal-observation objective optical system 36B form respective optical images with different optical characteristics on the common solid-state image-pickup element 7, thereby constituting the first and second image pickup means 8A and 8B.

The magnified-observation objective optical system 36A is used to magnify part of an image of the observation range θ2 obtained by the normal-observation objective optical system (or the wide-range-observation objective optical system) 36B, thereby obtaining an enlarged observation image. As shown in FIG. 3, the vertically long solid-state image pickup element 7 is disposed in accordance with the vertical arrangement of the objective optical systems 36A and 36B. On both sides of the solid-state image pickup element 7, a plurality of, e.g., two illuminating means 43 are arranged so as to sandwich the solid-state image pickup element 7. The illuminating means 43 each have a light emitting unit 42 for providing main illumination (i.e., emitting light, whose amount is larger than that of light emitted by each light emitting unit 34).

Referring to FIG. 1, the illuminating means 5 includes the illuminating means 43 and the ring-shaped illuminating means 35.

As shown in FIG. 2, the solid-state image pickup element 7 is mounted on one surface (front surface) of an image pickup board 44. The illuminating means 43 is also mounted on the image pickup board 44. In addition, the ring-shaped illumination board 33 is also connected to the image pickup board 44 via a lead wire or the like.

An IC chip and electronic components are mounted on the rear surface of the image pickup board 44, thus forming a signal processing and control unit 9a for performing signal processing on signals of the solid-state image pickup element 7 and controlling respective circuits in the capsule type endoscope 2. The signal processing and control unit 9a corresponds to the control means 9 in FIG. 1.

On the rear side of the image pickup board 44, e.g., a power supply board 45 is disposed. On one surface of the power supply board 45, a memory 11a, serving as the recording means 11, and another memory 11b, serving as the storage means 13, are mounted in addition to the switch 14.

The power supply board 45 is electrically connected to the image pickup board 44 via, e.g., a flexible board 46. The power supply board 45 is further connected to batteries 15a through the flexible board 46 extending to the rear side of the power supply board 45. The batteries 15a are arranged on the rear side of the power supply board 45 and correspond to the power supply means 15 in FIG. 1.

The flexible board 46 is electrically connected to a radio board 12a, which is arranged on the rear side of the batteries 15a. An IC chip and electronic components are mounted on the radio board 12a, thus forming a radio transmitting circuit 12b.

According to the present embodiment, data of images captured by the first and second image pickup means 8A and 8B arranged in the capsule type endoscope 2 is transmitted to the outside of the body via radio. The captured images are displayed on the display monitor 27 as shown in FIG. 5 and the like which will be described later.

The operation of the system with the above-described structure according to the present embodiment will now be described with reference to FIGS. 4A and 4B. The description will be made using mainly the components in FIG. 1. FIG. 4A is a flowchart showing the operation of the capsule type endoscope 2. FIG. 4B is a flowchart showing the operation of the extracorporeal device 3.

As shown in step S1, the switch 14 of the capsule type endoscope 2 is turned on to start power supply to the respective components from the power supply means 15 of the capsule type endoscope 2, thus activating the capsule type endoscope 2. The switch 14 is a magnetically-sensitive switch, e.g., a reed switch. After the capsule type endoscope 2 is inserted into the body cavity, a magnetic field is externally applied to the capsule type endoscope 2, thus turning on the switch 14.

In step S2, previously stored instruction data for the operation is transferred from the storage means 13 to the control means 9. Alternatively, the control means 9 reads previously stored instruction data for the operation from the storage means 13. The control means 9 controls illumination and image pickup in accordance with the instruction data as follows.

In step S3, the control means 9 first sets the illuminating means 5 and the first image pickup means 8A or the second image pickup means 8B to the operating state in accordance with the instruction data from the storage means 13.

After the illuminating means 5 and the first image pickup means 8A and the second image pickup means 8B are set in the operating state in step S3, as shown in step S4, illumination and image pickup are performed in accordance with data regarding an image pickup procedure included in the instruction data previously stored in the storage means 13. Captured images are generated, i.e., obtained.

Subsequently, analog signals of the captured images are converted into digital image data and the image data is sequentially recorded on the recording means 11 in time series as shown in step S5. In this case, information regarding the kind of the capsule type endoscope 2 and an identification code, serving as identification information, indicative of the type of image pickup means used for image pickup, i.e., either the first image pickup means 8A or the second image pickup means 8B in the capsule type endoscope 2 are added to image data to be recorded. Information regarding image pickup time may also be recorded.

In step S6, the image data recorded on the recording means 11 is sequentially transmitted (together with the identification codes) to the radio transmitting means 12. The radio transmitting means 12 high-frequency modulates the data and transmits the resultant data to the outside of the capsule type endoscope 2.

As shown by a dashed line of FIG. 4A, step S5 may be skipped. In other words, image data may be transferred (together with the identification codes) to the radio transmitting means 12 without being recorded on the recording means 11 and may be transmitted by radio. Therefore, the control means 9 and the recording means 11, alternatively, the control means 9 and the radio transmitting means 12 constitute recording/transmitting means for recording or transmitting captured image data in time series.

On the other hand, as shown in step S11, the extracorporeal device 3 receives radio signals, serving as image data, transmitted by radio from the radio transmitting means 12 of the capsule type endoscope 2 through the radio receiving means 23, demodulates the data, and then transmits the demodulated data to the extracorporeal recording means 24.

In step S12, the extracorporeal recording means 24 adds information regarding time when the demodulated data has been received, information indicative of the kind of the capsule type endoscope 2, and the identification code and the like to the demodulated image data and records the data on a hard disk or the like in time series.

As shown in step S13, the extracorporeal recording means 24 transmits the image data to the display unit 22 by wireless or wire. In step S14, the extracorporeal recording means 24 transmits the information indicative of the kind of the capsule type endoscope 2 and the instruction data regarding the image pickup procedure to the display control means 28.

The display control means 28 can receive instruction data regarding a display method, the data being entered by a user (operator) through the display-method input unit 29. When instruction data regarding a display method is not supplied from the display-method input unit 29, the display control means 28 controls a display method in accordance with the descriptions of the instruction data regarding the image pickup procedure. Information regarding a display method different from the descriptions of the instruction data regarding the image pickup procedure may be previously stored in the storage means 13. Data regarding the different display method may be added to the instruction data regarding the image pickup procedure. A display method may be controlled in accordance with the resultant instruction data.

In step S15, the display control means 28 transmits the instruction data regarding the display method to the operation control means 26. Therefore, the method for displaying different image data is controlled in accordance with an instruction from the display control means 28. In other words, the display method can be changed. The descriptions of the instruction depend on information stored in the storage means 13 or information supplied from the display-method input unit 29.

In step S16, the display monitor 27 displays images. In this case, as shown in FIG. 5 or 6, images are displayed on the display monitor 27 in accordance with instruction data regarding a display method or instruction data regarding an image pickup procedure. For example, when the instruction data regarding the display method is not entered through the display-method input unit 29, images can be displayed in accordance with the instruction data regarding the image pickup procedure previously stored in the storage means 13.

FIG. 5 shows an example of a display method in the case where the user enters an instruction regarding the display method on the display-method input unit 29.

According to the display method shown in FIG. 5, a normal-observation image display area 51 and a magnified-observation image display area 52 are arranged in left and right portions on the display screen of the display monitor 27. With this arrangement, a normal observation image captured by the normal-observation objective optical system 36B and a magnified observation image captured by the magnified-observation objective optical system 36A are simultaneously displayed adjacent to each other.

In addition, an information display area 53 is arranged below the magnified-observation image display area 52 in the upper right portion. In the information display area 53, information concerning transmit time of the capsule type endoscope 2 in the body cavity and positional information of the capsule type endoscope 2 in the body cavity are displayed. In the normal-observation image display area 51, a range 51a for magnified observation by the magnified-observation objective optical system 36A is shown by a broken line such that the user, such as a medical staff, can easily understand the relation between a normal observation image and a magnified observation image.

In this case, an image pickup sequence, included in the instruction data stored in the storage means 13 of the capsule type endoscope 2, ensures alternate capturing of normal observation images and magnified observation images by the second image pickup means 8B (normal-observation objective optical system 36B) and the first image pickup means 8A (magnified-observation objective optical system 36A).

In other words, the first and second image pickup means 8A and 8B alternately capture images in the following order: the second image pickup means 8B→the first image pickup means 8A→the second image pickup means 8B→the first image pickup means 8A→ . . .

In the extracorporeal device 3, received images are temporarily stored in a memory for normal image storage and a memory for magnified image storage. As shown in FIG. 5, the images are displayed in the display areas 51 and 52. When a new image is received, the corresponding memory is updated using image data of the received image and a display image is also updated.

As shown in FIG. 5, a normal image and a magnified image can simultaneously be displayed. Since the user, such as a medical staff, can observe both the images, this display method ensures that a diagnosis can be easily made. In addition, since the system is provided with the display-method input unit 29, images can be displayed so that the user can easily make a diagnosis.

FIG. 6 shows an example of another display method whereby images are sequentially displayed in accordance with an image pickup procedure stored in the storage means 13.

In this case, normal observation images and magnified observation images are displayed on the display screen of the display monitor 27 such that the image pickup procedure is reflected to an image to be displayed. In this case, the image pickup means are used in accordance with the image pickup procedure in the following order: the second image pickup means 8B→the second image pickup means 8B→the first image pickup means 8A→the second image pickup means 8B→the second image pickup means 8B→the first image pickup means 8A→ . . .

According to this display method shown in FIG. 6, therefore, normal observation images 6(A) and 6(B) are successively displayed and, after that, a magnified observation image 6(C) is displayed. Then, normal observation images 6(D) and 6(E) are successively displayed and, after that, a magnified observation image 6(F) is displayed. According to this display method, information indicating whether the currently displayed image is a normal observation image or a magnified observation image (e.g., "NORMAL" in the case of a normal observation image and "MAGNIFIED" in the case of a magnified observation image in FIG. 6) may be displayed on the display screen such that an observer can easily grasp a state of the currently displayed image (display mode). In this case, in each normal observation image, a range of the corresponding magnified observation image is shown by a broken line so that the relation between both the images can easily be understood. According to this display method, therefore, the medical staff can easily make a diagnosis.

As for the display screen of the display monitor 27, for example, a first display monitor unit 54 and a second display monitor unit 55 may be arranged laterally as shown in FIG. 7 such that the normal-observation image display area 51 and the magnified-observation image display area 52 are simultaneously displayed. Referring to FIG. 7, the first display monitor unit 54 is integrated with the second display monitor unit 55, thus forming the display monitor 27. The first display monitor unit 54 may be separated from the second display monitor unit 55. In other words, different kinds of observation images may be displayed on separated display monitors.

Any of the display methods shown in FIGS. 5 to 7 is a typical display example. Another display method may be used to display images.

As described above, according to the present embodiment, two kinds of image pickup means 8A and 8B focus optical images on the common solid-state image pickup element 7. With this arrangement, the capsule type endoscope 2 can be miniaturized. In addition, information regarding a display method can be previously set in the capsule type endoscope 2 and images can be displayed by the display method. Alternatively, the user can input data regarding a display method so that images are displayed by the display method suitable for diagnosis. Advantageously, in the use of the different kinds of image pickup means 8A and 8B, images can be displayed so that a diagnosis can be easily made.

In addition, since the different kinds of image pickup means 8A and 8B are built in the endoscope, the capability to facilitate a diagnosis can be improved compared with that of a capsule type endoscope having only one image pickup means. For instance, a diagnosis can be made more closely using the capsule type endoscope including the magnified-observation image pickup means in addition to the normal-observation image pickup means than a capsule type endoscope including only normal-observation image pickup means.

Since the relation between observation ranges of different kinds of images is also displayed, the user can easily understand the images according to the display method. Thus, the system suitable for a diagnosis can be provided. Accordingly, the capability to facilitate a diagnosis based on one passage examination of the capsule type endoscope 2 can be remarkably improved. A display method can be appropriately set. Thus, a diagnosis can efficiently be established.

When image data captured by the capsule type endoscope 2 is transmitted to the extracorporeal device 3, an identification code is added to the data. Even when set image pickup procedures vary with capsule type endoscopes 2, images can be displayed according to a display method based on the corresponding image pickup procedure. When different display methods are set in respective capsule type endoscopes 2 (by, e.g., different users), images can be displayed faithfully to the corresponding set display method.

Second Embodiment

Figure 8A:
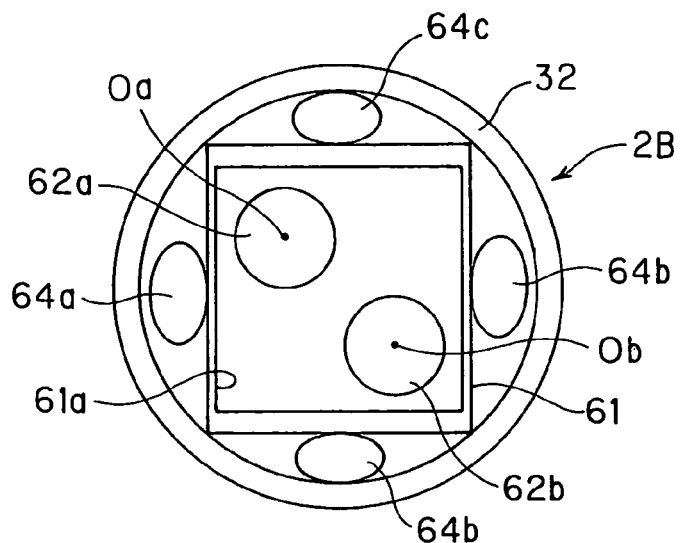
FIG. 8A is a schematic diagram showing the structure of a capsule type endoscope according to a second embodiment of the present invention, as viewed in the direction shown by the arrow A.
Figure 8B:
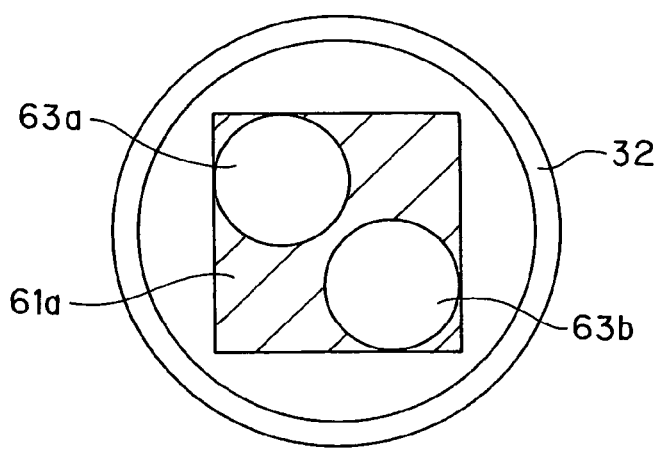
FIG. 8B is a diagram showing the structure of image pickup means of the capsule type endoscope according to the second embodiment and an area actually used for image pickup by a solid-state image pickup element.
Figure 9:
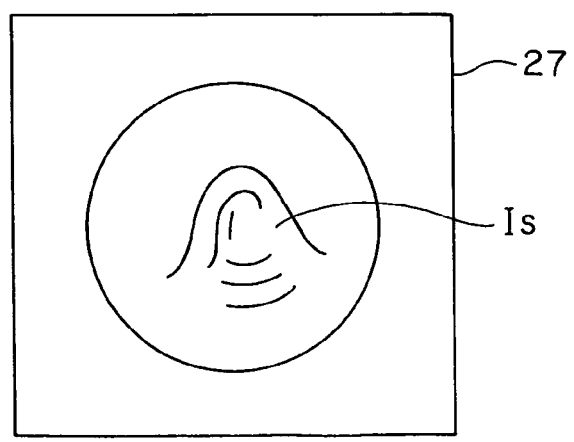
FIG. 9 is a diagram showing a display example in which a stereoscopic image is displayed.

A capsule type endoscope according to a second embodiment of the present invention will now be described with reference to FIGS. 8 and 9. FIG. 8A is a schematic diagram showing the structure of a capsule type endoscope 2B, except for a tip cover, as viewed in the direction shown by the arrow A. FIG. 8B is a diagram showing an area actually used for image pickup by a solid-state image pickup element of the capsule type endoscope 2B.

The capsule type endoscope 2B includes a substantially square solid-state image pickup element 61 instead of the vertically long solid-state image pickup element 7 in the foregoing capsule type endoscope 2 shown in FIGS. 2 and 3. The solid-state image pickup element 61 has a square light receiving surface (image pickup surface) 61a. In front of the solid-state image pickup element 61, objective optical systems 62a and 62b of the same type, e.g., each corresponding to the normal-observation objective optical system 8B, are arranged next to each other.

In this case, as shown in FIG. 8A, those two objective optical systems 62a and 62b are disposed next to each other along the diagonal of the square light receiving surface 61a of the common solid-state image pickup element 61. Reference symbols Oa and Ob denote the optical axes of the objective optical systems 62a and 62b, respectively.

As shown in FIG. 8B, the objective optical systems 62a and 62b focus optical images on the square light receiving surface 61a such that the optical images are formed in optical-image formation areas 63a and 63b arranged along the diagonal of the surface 61a. In other words, images of substantially the same portion are captured using the two objective optical systems 62a and 62b having the same characteristics with different angles (of center axes of view), whereby stereoscopic-observation optical images with binocular parallax are formed on the common solid-state image pickup element 61. In FIG. 8B, a hatched portion denotes an unused area.

Referring to FIG. 8A, illumination light emitting elements 64a and 64b are arranged on the left and right sides of the solid-state image pickup element 61. In addition, illumination light emitting elements 64c and 64d are arranged on the upper and lower sides thereof. Those elements simultaneously emit light. Image pickup is performed simultaneously with light emission.

Image signals captured by the solid-state image pickup element 61 are transmitted to an extracorporeal device 3 placed on the outside of a body. In the extracorporeal device 3, image data captured by the two objective optical systems 62a and 62b is subjected to image combination processing to generate a three-dimensional image. As shown in FIG. 9, a display monitor 27 displays a three-dimensional image (stereoscopic image) Is.

According to the present embodiment, since a three-dimensional image is obtained, information to easily recognize the state of a lesion, e.g., irregularities on the surface of the lesion, can be obtained. An image captured by one objective optical system (e.g., 62a) and the three-dimensional image Is may be alternately displayed at predetermined time intervals.

Third Embodiment

Figure 10A:
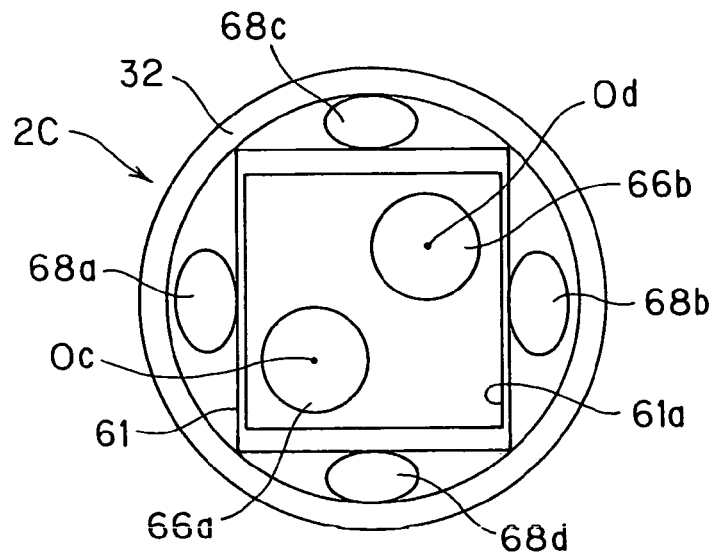
FIG. 10A is a schematic diagram showing the structure of a capsule type endoscope according to a third embodiment of the present invention, except for a tip cover, as viewed along the arrow A.
Figure 10B:
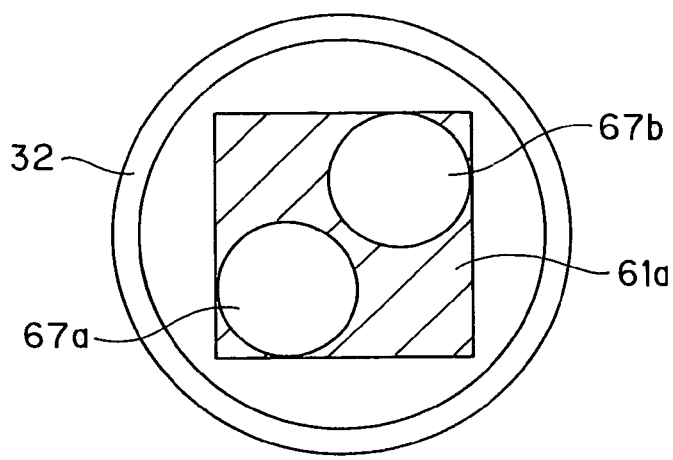
FIG. 10B is a diagram showing an area actually used for image pickup by a solid-state image pickup element of the capsule type endoscope according to the third embodiment.

FIG. 10A is a schematic diagram showing the structure of a capsule type endoscope 2C according to a third embodiment of the present invention, except for a tip cover, as viewed in the direction shown by the arrow A. FIG. 10B is a diagram showing an area actually used for image pickup by a solid-state image pickup element of the capsule type endoscope 2C. The present capsule type endoscope 2C has a solid-state image pickup element 61 similar to that of the capsule type endoscope 2B shown in FIGS. 8A and 8B and includes two objective optical systems 66a and 66b arranged along the diagonal of a square light receiving surface 61a of the element 61.

In this case, as shown in FIG. 10B, the objective optical systems 66a and 66b form optical images in optical-image formation areas 67a and 67b along the diagonal of the square light receiving surface 61a. This arrangement realizes a reduction in the size of the light receiving surface 61a. In FIG. 10B, a hatched portion corresponds to an unused area.

Referring to FIG. 10A, illumination light emitting elements 68a and 68b are arranged on the left and right sides of the solid-state image pickup element 61. In addition, illumination light emitting elements 68c and 68d are arranged on the upper and lower sides thereof.

According to the present embodiment, the light emitting elements 68a and 68d emit, e.g., white light and the other light emitting elements 68b and 68c emit light having a narrow-band wavelength so as to obtain a special-light observation image at the narrow-band wavelength. A wavelength having such properties that a living body selectively absorbs light with the wavelength in a visible region, or another wavelength having such properties that tissue of a lesion selectively absorbs light with the wavelength may be used. Alternatively, light having a wavelength in the infrared region may be used so that information about deep part can be obtained. The light emitting elements 68a and 68d and the other light emitting elements 68b and 68c are controlled so that the elements alternately emit light intermittently at different times.

In the use of a CCD as a solid-state image pickup element 7, providing that illumination with white light and illumination with light having a wavelength in the narrow band are alternately performed intermittently and normal image pickup and special-light image pickup are alternately performed, control means 9 controls illumination such that captured image signals are transferred from the light receiving surface 61a of the solid-state image pickup element 7 to a transfer unit before the next illumination starts, alternatively, captured image signals are read from the solid-state image pickup element 7 and, after that, the next illumination is performed. According to the present embodiment, one illumination is performed and, after that, signals are read from the solid-state image pickup element 7 before the next illumination starts.

In this case, signal charge in the area 67a or 67b, which is not used, is not used in recording and is not transmitted. For example, in normal image pickup using white illumination, signal charge in the area 67a is recorded or transmitted. However, signal charge in the area 67b is not used in recording or transmission. In image pickup using illumination with a wavelength in the narrow band, signal charge in the area 67a and that in the area 67b are processed in a manner opposite to the above.

Figure 11:
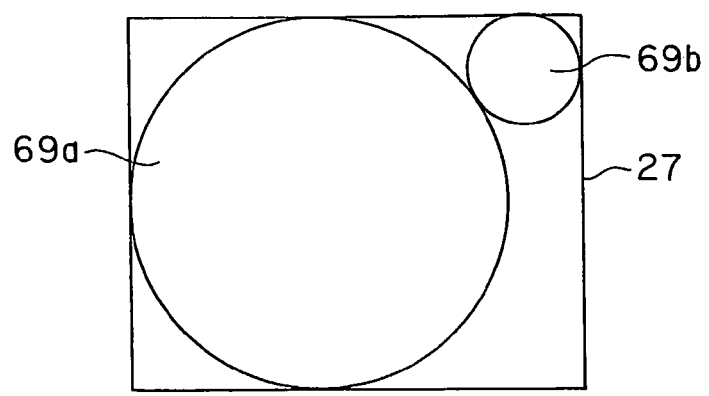
FIG. 11 shows a display example in which two kinds of images are simultaneously displayed on the display monitor.

FIG. 11 shows a display example in a display monitor 27 according to the present embodiment. In the present embodiment, for example, a normal observation image is displayed in a large normal-observation image display area 69a and a special-light observation image is displayed in a small special-light observation image display area 69b.

A normal observation image and a magnified observation image described in the first embodiment may be displayed as shown in FIG. 11.

In the case where different kinds of image data captured during intermittent light emission are stored in extracorporeal recording means in time series and are then sequentially read and displayed in order to observe the images, the images may be successively displayed in the areas 69a and 69b at a high rate of 20 frames per second in accordance with, e.g., a display method designated by a user.

Figure 12:
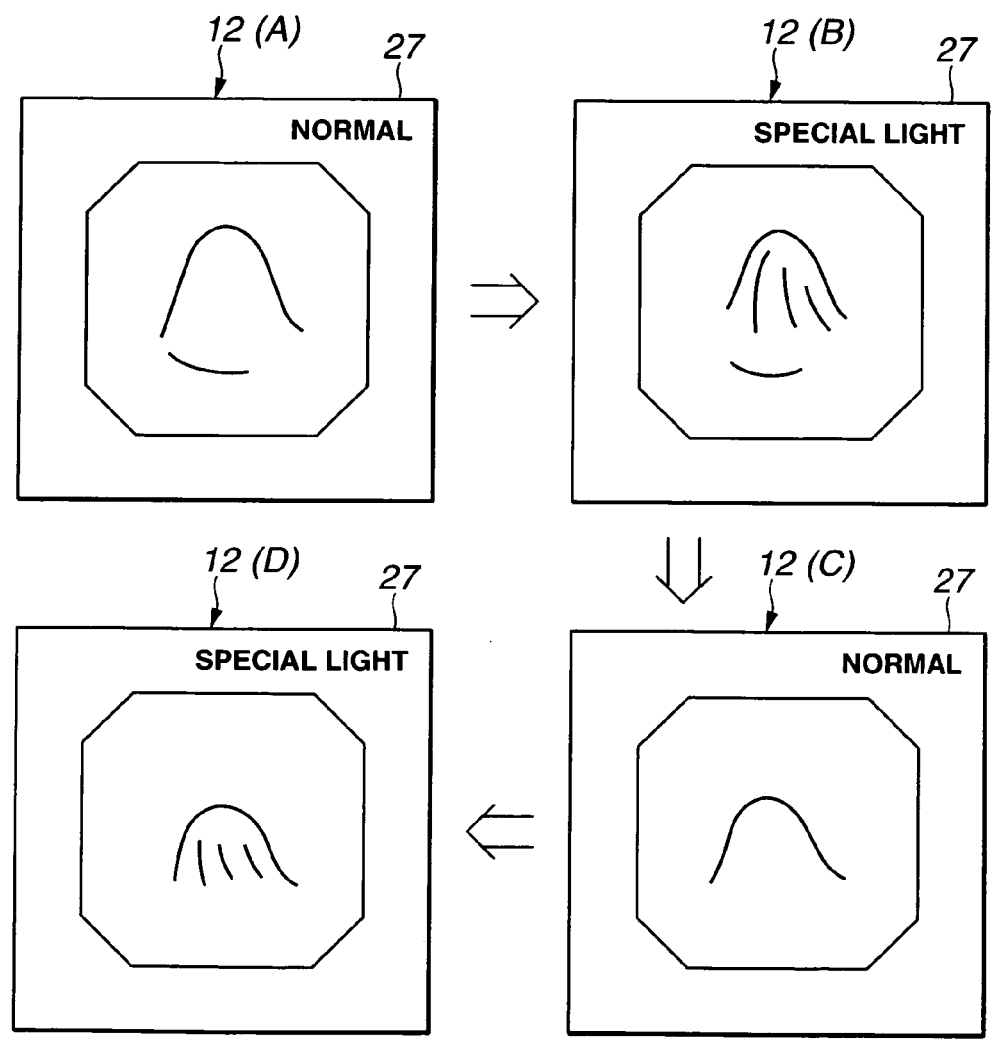
FIG. 12 shows a display example in which two kinds of images are alternately displayed on the display monitor.

Depending on a selected display method, normal observation images and special-light observation images can be alternately displayed on the display screen of the display monitor 27 as shown by observation images 12A to 12D in FIG. 12. In other words, observation images are displayed in the following order: normal light→special light (narrow band light) →normal light→special light (narrow band light), . . . In this case, information, e.g., "NORMAL" or "SPECIAL LIGHT", may be displayed so that the user can easily understand the current display mode.

Observation images are not necessarily displayed alternately as shown in FIG. 12. Images may be displayed in accordance with a predetermined alternate display pattern, e.g., in the following order: normal light→normal light→special light (narrow band light)→normal light→normal light→special light (narrow band light) . . .

According to the present embodiment, normal observation images and observation images captured using special light can be obtained. Thus, the capability to facilitate a diagnosis can be further improved.

As for special light, excitation light used for fluorescent observation may be generated. Fluorescent observation may be performed using the excitation light. Accordingly, the present system may be applied to fluorescent observation. More specifically, narrow band observation, infrared observation, and fluorescent observation may be performed as the above-described special light observation.

Fourth Embodiment

The structure of a capsule type medical system according to a fourth embodiment of the present invention will now be described. This capsule type medical system includes capsule type endoscopes 2D and 2E shown in FIGS. 13 and 14 and an extracorporeal device 3B shown in FIG. 15. First, the structures of the capsule type endoscopes 2D and 2E will now be described with reference to FIGS. 13 and 14.

Figure 13:
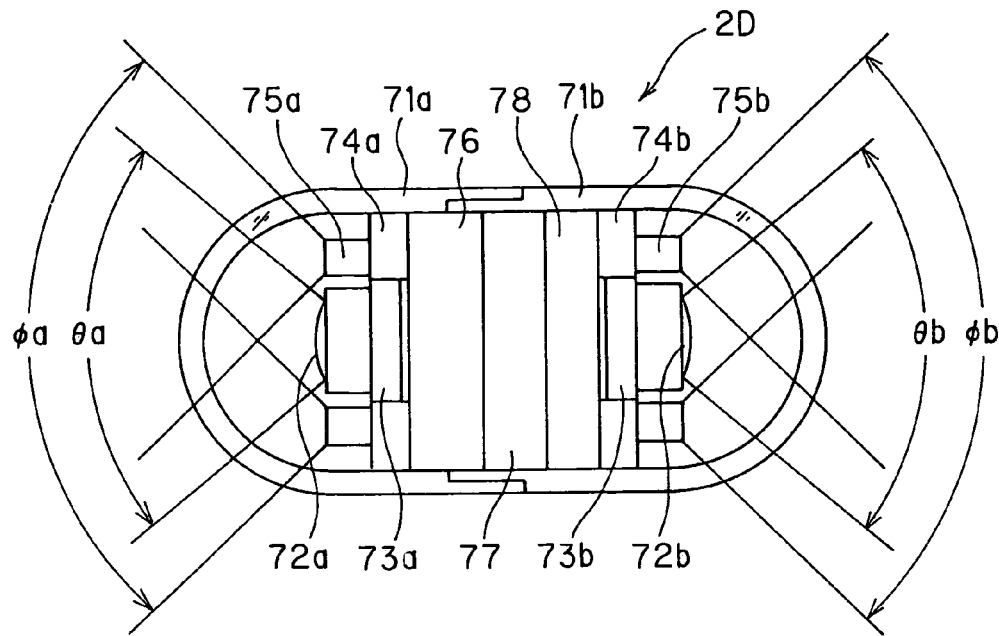
FIG. 13 is a vertical sectional view of the structure of a first capsule type endoscope constituting a system according to a fourth embodiment of the present invention.

FIG. 13 is a schematic vertical sectional view of the structure of the first capsule type endoscope 2D according to the fourth embodiment of the present invention. The present capsule type endoscope 2D includes a plurality of illuminating means and a plurality of image pickup means arranged at the front and rear portions to obtain a forward image (forward direct view image) and a backward image (backward direct view image).

Semispherical transparent covers 71a and 71b are engaged with each other at tubular open-ends of the respective covers, thus forming a capsule type airtight container.

In the airtight container, an objective optical system 72a attached to a lens frame is disposed in the center so as to oppose to the inner top of the cover 71a. An image pickup unit 73a including a solid-state image pickup element is mounted on an LED board 74a such that the unit 73a is located at the image forming position of the system 72a. On the LED board 74a, a plurality of LEDs 75a are mounted around the objective optical system 72a, thus forming an illumination unit.

Similarly, an objective optical system 72b attached to a lens frame is disposed in the center so as to oppose to the inner top of the cover 71b. An image pickup unit 73b including a solid-state image pickup element is mounted on an LED board 74b such that the unit 73b is located at the image forming position of the system 72b. On the LED board 74b, a plurality of LEDs 75b are mounted around the objective optical system 72b, thus forming an illuminating unit.

On the rear side of the LED board 74a, a drive and control circuit 76 for driving the image pickup units 73a and 73b and controlling other circuits, a power supply 77 and a radio circuit 78 are disposed. In the drive and control circuit 76, a nonvolatile memory, such as an EEPROM, for storing information regarding image pickup procedures is arranged.

Reference symbol θa denotes a forward observation range of the objective optical system 72a and the image pickup unit 73a. An illumination range φa of the illuminating unit including the LEDs 75a is set to be larger than the observation range θa.

Similarly, reference symbol θb denotes a backward observation range of the objective optical system 72b and the image pickup unit 73b. An illumination range φb of the illuminating unit including the LEDs 75b is set to be larger than the observation range θb.

For instance, the observation ranges θa and θb are set to be different from each other. The capsule type endoscope 2D captures, e.g., forward and backward images alternately and transmits image data by radio to the outside through the radio circuit 78. When transmitting image data, the capsule type endoscope 2D adds an identification code to the data and then transmits the resultant data. In addition, an image pickup procedure for capturing images twice in one direction and capturing an image once in the other direction may be set (i.e., stored in the above-mentioned nonvolatile memory).

Figure 14:
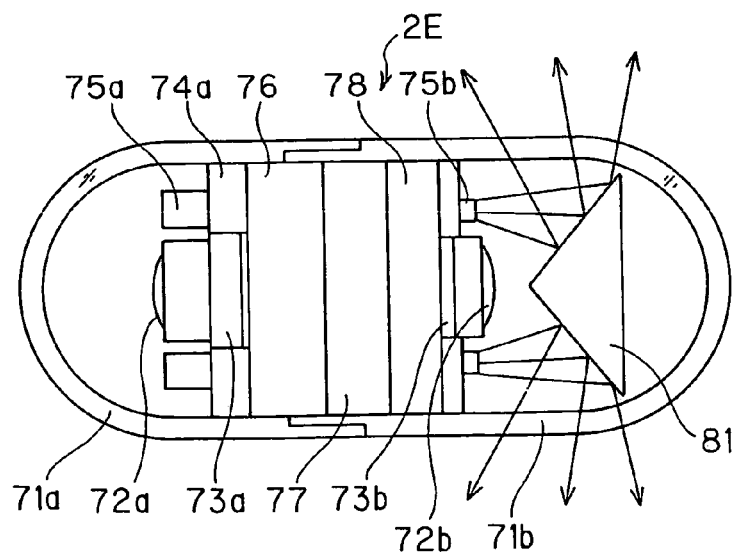
FIG. 14 is a vertical sectional view of the structure of a second capsule type endoscope constituting the system according to the fourth embodiment.

FIG. 14 is a schematic vertical sectional view of the structure of the second capsule type endoscope 2E according to the fourth embodiment. The present capsule type endoscope 2E has substantially the same structure as that of the capsule type endoscope 2D in FIG. 13, except that one image pickup means is modified. For example, the backward image pickup means in FIG. 13 is modified such that a conical optical element 81 is arranged such as to fundamentally face the objective optical system 72b.

As described above, the conical optical element 81 for reflecting light at the conical surface is opposed to the objective optical system 72b such that the apex of the optical element 81 is aligned to the optical axis of the objective optical system 72b. Thus, as shown in FIG. 14, light emitted from the LEDs 75b is reflected by the opposed optical element 81, so that reflected rays are directed in all around directions substantially perpendicular to the center axis of the capsule type endoscope 2E, i.e., the rays are allowed to exit from side part thereof. Thus, areas in the all around directions are illuminated and an optical image in the all around directions is formed on the image pickup unit 73b. As for an image to be formed, an optical image in one direction may be formed using part of the conical optical element, alternatively, an optical image in substantially all around directions may be formed.

The capsule type endoscope 2E performs forward (direct view) image pickup and all around (side) image pickup in accordance with a predetermined rule and transmits captured image data by radio to the outside.

For example, according to a periodic image pickup procedure, an image may be captured once in the forward direction and, after that, an image may be captured two or three times in the all around directions.

In FIGS. 13 and 14, a memory may be arranged instead of the radio circuit 78. Captured image data may be stored in the memory. To store data in the memory, an identification code is first recorded and information about image pickup time and information concerning the (forward or backward) image pickup unit used are written to each image data. Alternatively, both of the radio circuit 78 and the memory may be disposed so that image data obtained by forward image pickup and that obtained by all around (side) image pickup are recorded on the memory in a time sharing manner and the data is transmitted by radio to the outside of the body. In transmitting image data, an identification code of the capsule type endoscope 2E is added to the data and the resultant data is then transmitted.

Figure 15:
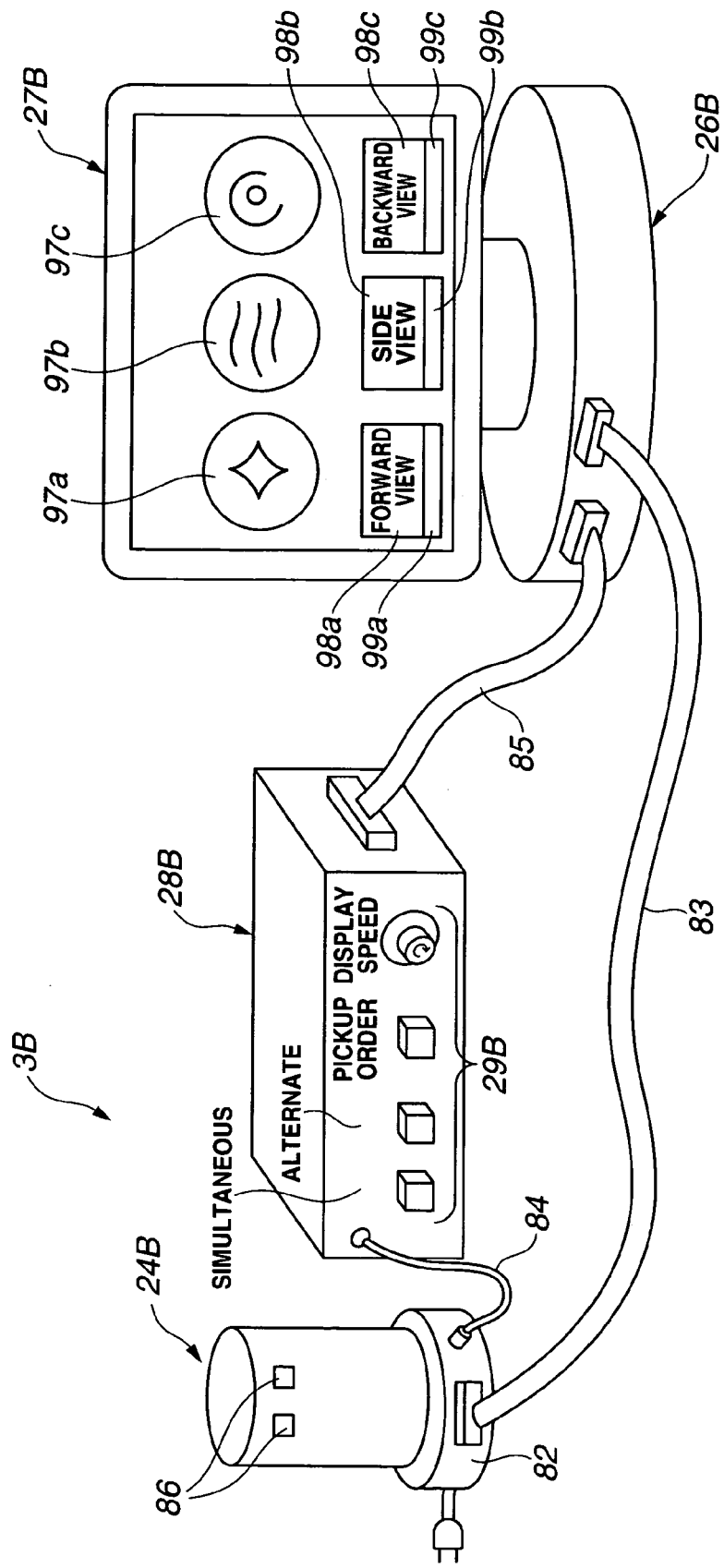
FIG. 15 is a perspective view of the structure of an extra-corporeal device constituting the system according to the fourth embodiment.

FIG. 15 shows the structure of the extracorporeal device 3B according to the present embodiment. The extracorporeal device 3B includes: an extracorporeal recorder 24B, serving as extracorporeal recording means, having therein radio receiving means and a flash memory (hereinafter, the extracorporeal recorder 24B will be referred to as extracorporeal recording means); a display controller 28B, serving as display control means, provided with a display-method input unit 29B at the front surface (hereinbelow, the display controller 28B will be referred to as display control means); a display monitor 27B incorporated with an operation controller 26B, serving as operation control means (hereinbelow, the operation controller 26B will be referred to as operation control means); and a cradle 82 on which the extracorporeal recording means 24B is detachably mounted.

When being attached to the cradle 82, the extracorporeal recording means 24B can be operated with commercial power supply. In addition, when an image transmission cable 83 is connected to a connector provided for the cradle 82, the cradle 82 is electrically connected to the operation control means 26B so that image data recorded on the flash memory of the extracorporeal recording means 24B can be transmitted to the operation control means 26B.

The extracorporeal recording means 24B is connected to the display control means 28B via a transmission cable 84 connected to the cradle 82 so that information can be transmitted from the storage means of the capsule type endoscope 2D or 2E to the display control means 28B through the transmission cable 84.

The display control means 28B is electrically connected to the operation control means 26B via a connection cable 85 so that information regarding a display method input from the display-method input unit 29B can be transmitted to the operation control means 26B.

On the outer surface of the extracorporeal recording means 24B, for example, LEDs 86 are arranged as receiving-state display means.

A display monitor 27B displays images captured by the capsule type endoscopes 2D and 2E in accordance with a display method based on settings entered on the display-method input unit 29B. The display-method input unit 29B includes, e.g., a button to instruct a simultaneous display mode, a button to instruct an alternate display mode, a button to instruct a pickup-order display mode for displaying images in the order of image pickup, and a knob to change a display speed.

The display monitor 27 in FIG. 15 is compatible with the capsule type endoscopes 2D and 2E. In a display example of FIG. 15, images captured by the two capsule type endoscopes 2D and 2E are displayed in combination.

In a display screen of the display monitor 27, forward-view, side-view, and backward-view display areas 97a, 97b, and 97c are set so that images captured by the forward, side, and backward image pickup units can be simultaneously displayed.

Below the display areas 97a, 97b, and 97c, display portions 98a, 98b, and 98c each indicating which image pickup unit has been used for image pickup are arranged. Under the display portions 98a, 98b, and 98c, display portions 99a, 99b, and 99c to display information indicating the image capturing (image pickup) time, the image number and the like are arranged.

According to the present embodiment, in the use of the different kinds of capsule type endoscopes 2D and 2E, images can be displayed by display methods suitable for the respective kinds of capsule type endoscopes so that the user can easily make a diagnosis or easily understand the images. Even when capsule type endoscopes of the same kind are used, images can be displayed by a display method using identification codes of the endoscopes so that the user can easily make a diagnosis or easily understand the images.

In the use of the capsule type endoscopes 2D and 2E having different observation ranges θa and the like, image pickup omission can be substantially solved or remarkably reduced to sufficiently obtain necessary image information during one passage examination. In addition, images can be appropriately displayed in accordance with the kinds of image pickup means so that a diagnosis can be easily made.

In the above description, the case of using the two capsule type endoscopes 2D and 2E has been simply explained. The present system can also be widely applied to other capsule type endoscopes.

For example, when the orientation of the capsule type endoscope 2E of FIG. 14 is reversed and is then swallowed, the endoscope 2E serves as a side and backward view capsule type endoscope.

The present system can also be applied to an oblique view capsule type endoscope 2F and its body 102 shown in FIG. 16 which will be described later.

The present system can also be applied to a case where the capsule type endoscopes 2D and 2E in FIGS. 13 and 14 are used in one examination for the same patient.

Figure 16:
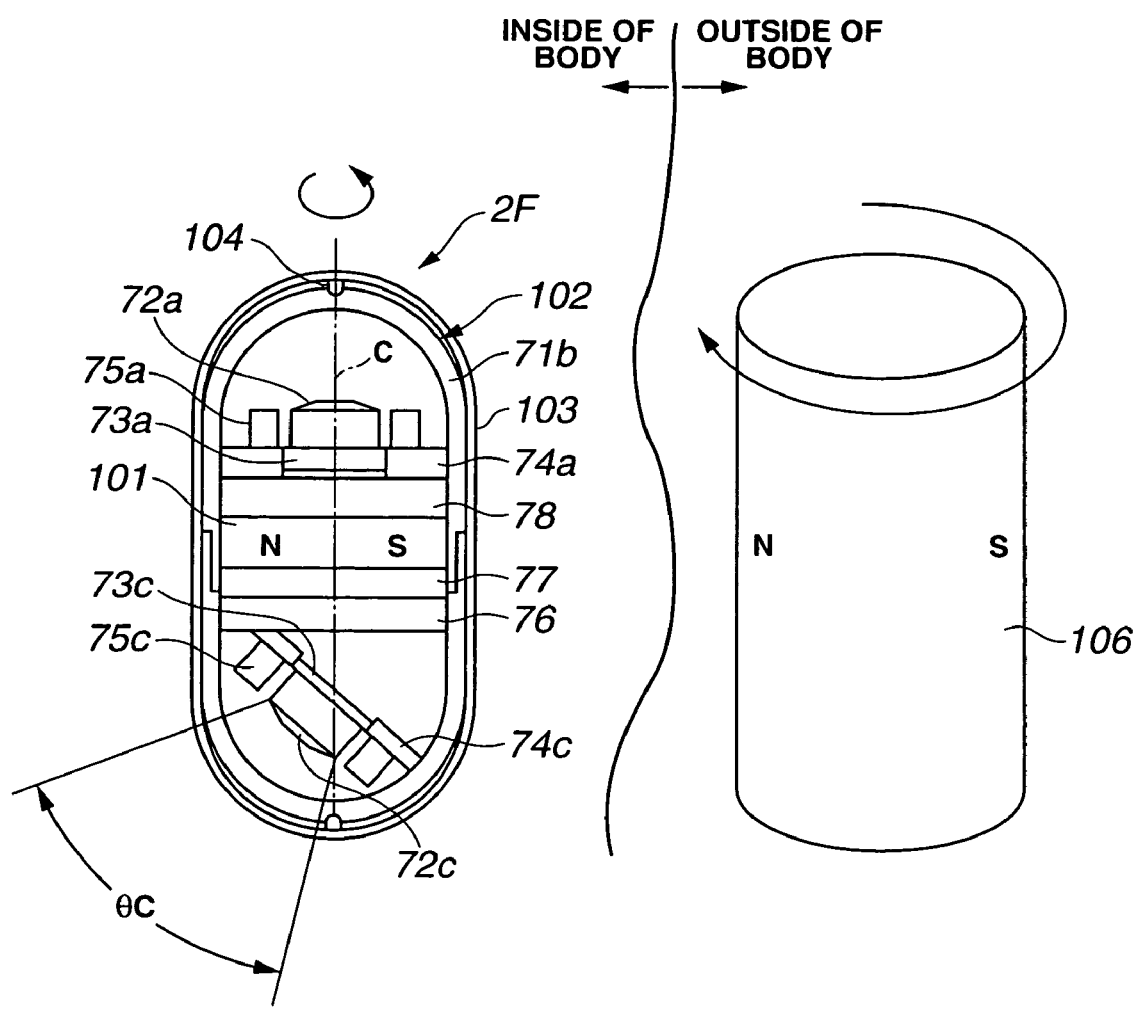
FIG. 16 is a diagram showing a capsule type endoscope and the like according to a first modification of the fourth embodiment.

FIG. 16 shows the structure of a capsule type endoscope 2F according to a first modification of the above-described embodiment and the structure of extracorporeal driving means for rotating the capsule type endoscope 2F.

The structure of the present capsule type endoscope 2F is obtained by modifying one image pickup means in, e.g., the capsule type endoscope 2D of FIG. 13. For instance, the components for backward viewing in FIG. 13 are modified to components for oblique viewing. In addition, a capsule type endoscope body 102 having therein a magnet 101 is disposed in a transparent outer case 103, and a pin 104 is arranged along a center axis C of the body such that the capsule type endoscope body is rotatable about the center axis C.

In the capsule type endoscope body 102, an objective optical system 72c, an image pickup unit 73c, LEDs 75c, and an LED board 74c are arranged obliquely compared to the components in the capsule type endoscope 2D of FIG. 13, thus providing an observation range θc for oblique viewing.

A rotatable magnet 106 is disposed outside a body. Rotating the magnet 106 causes the rotation of the capsule type endoscope body 102 to obtain all around observation images in oblique side directions. Images captured by the capsule type endoscope 2F can be displayed on the display monitor 27B of the extracorporeal device 3B. Therefore, the magnet 101 in the capsule type endoscope 2H and the rotatable magnet 106 constitute the rotating driving means for rotating the capsule type endoscope 2F about the center axis in the lengthwise direction of the capsule body.

According to the present modification, all around observation images in the oblique side directions can be obtained.

Figure 17:
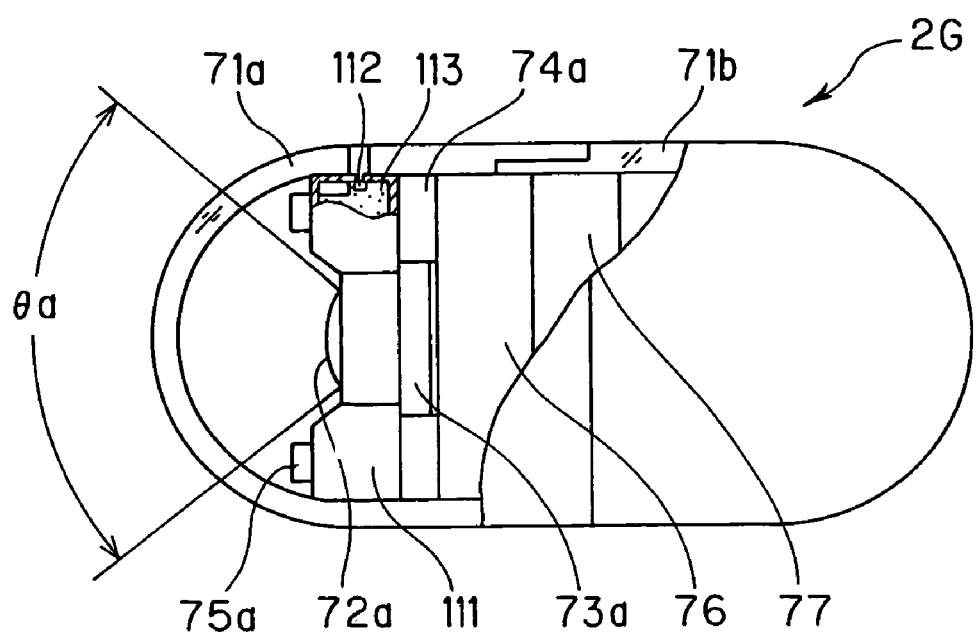
FIG. 17 is a partial vertical sectional view of a capsule type endoscope according to a second modification of the fourth embodiment.

FIG. 17 schematically shows the structure of a capsule type endoscope 2G according to a second modification. The present capsule type endoscope 2G is constructed by modifying, e.g., part of the forward view image pickup means of the capsule type endoscope 2D of FIG. 13 in such a manner that an agent storage tank 111 is disposed in the front of the LED board 74 and the LEDs 75a are arranged in the front of the agent storage tank 111.

In other words, the substantially annular agent storage tank 111 is arranged along the observation range θa such as to surround the objective optical system 72a. The agent storage tank 111 has a hole communicating with the outside and includes a valve 112 in the hole, the valve being switched from the closed position to the open position in response to an electric signal. When the valve 112 is opened, an agent 113 stored in the tank can be expelled. To expel the agent 113, for example, a signal is transmitted from the outside of a body, the valve 112 is opened by the drive and control circuit 76 through the radio circuit 78, thereby discharging, e.g., a hemostatic agent.

In this case, the use of the agent storage tank 111 has been described. A tank for storing a marker solution to highlight the area of interest can be used.

According to the present modification, the agent storage tank 111 is disposed in a space, serving as the dead space of the objective optical system 72a. Thus, the internal space of the capsule type endoscope 2G is effectively used.

When a patient takes such a capsule type endoscope with a transparent liquid such as abstergent so that underwater images can be captured during endoscopic observation of the small or large intestine, the liquid may be mixed with bile. Unfortunately, captured images may become yellowish. Such a problem can be prevented by the following solving means.

The solving means includes:
(1) Taking a mixture of the transparent liquid and anticholagogue (e.g., ethinylestradiol) with the capsule type endoscope;
(2) Disposing a blue filter for compensating yellow in the capsule type endoscope; and
(3) Image processing on captured images to reduce the intensity of the yellow component (on the basis of an image of the esophagus or stomach that is not influenced by bile).

Fifth Embodiment

Figure 18:
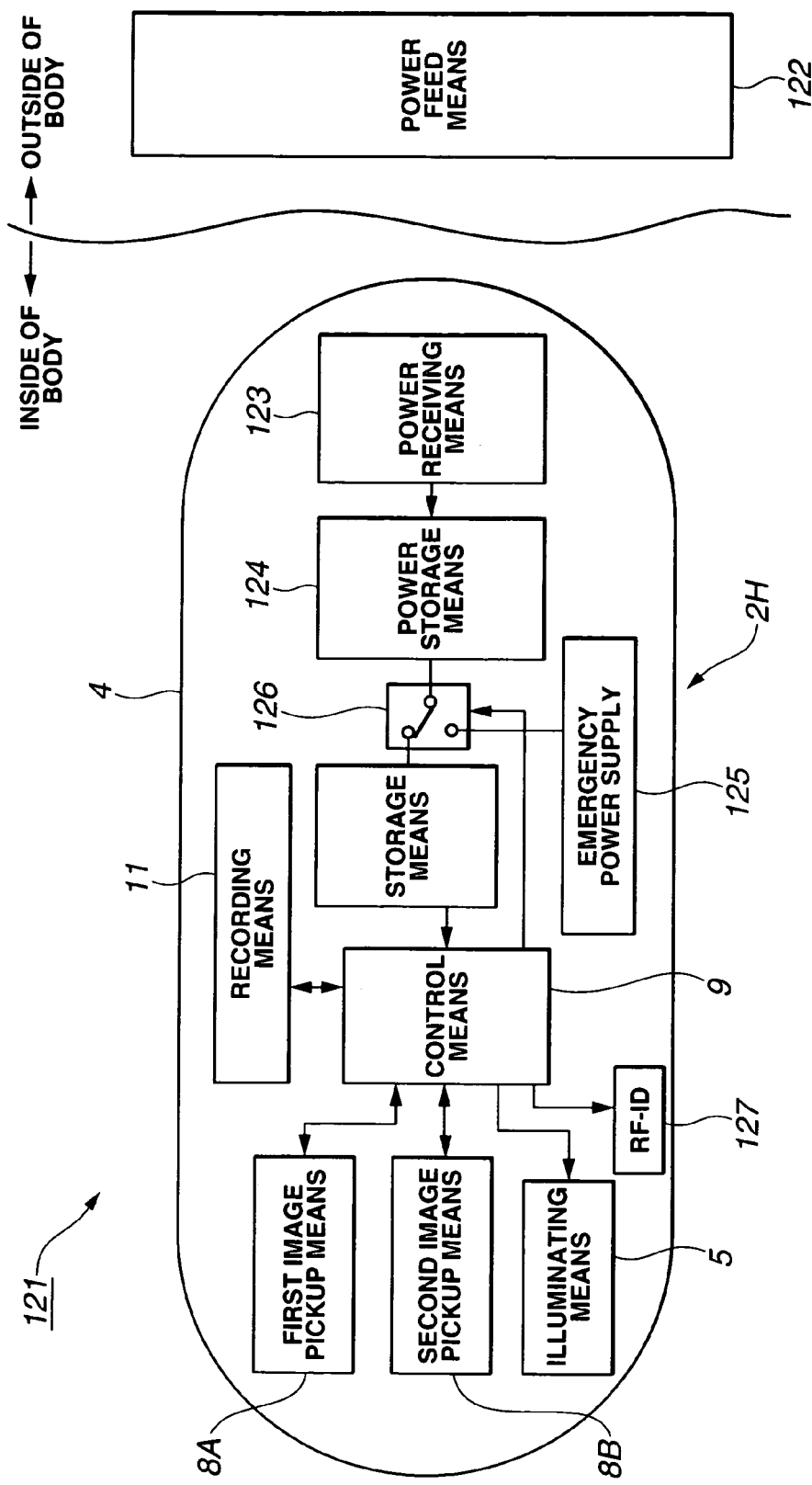
FIG. 18 is a diagram showing the structures of a capsule type endoscope and the like according to a fifth embodiment of the present invention.
Figure 19:
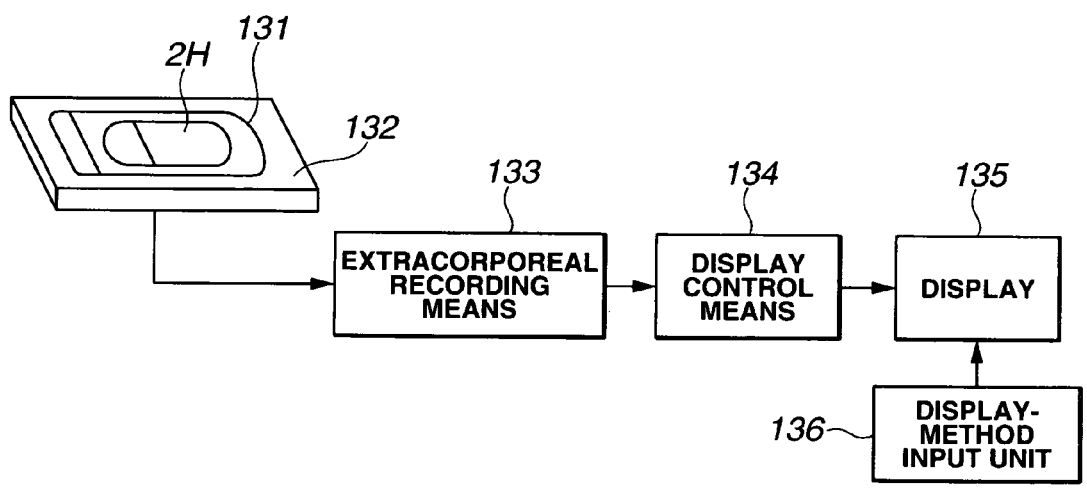
FIG. 19 is a diagram schematically showing a state where recorded information is read from the capsule type endoscope after recovery.

A fifth embodiment of the present invention will now be described with reference to FIGS. 18 and 19. FIG. 18 is a diagram showing the structure of a capsule type endoscope 2H during image pickup in vivo and the structure of external power feed means 122 for the endoscope 2H. FIG. 19 is a diagram showing the structure of a medical system 121 used to read image information stored in the capsule type endoscope 2H which has been excreted from a body and been recovered.

The capsule type medical system 121 uses the capsule type endoscope 2H configured to record (store) captured image data on recording means 11 without transmitting the data by radio like the capsule type endoscope 2 of FIG. 1, receive electrical energy supplied from the external power feed means 122 by wireless through power receiving means 123, and store the energy in power storage means 124.

The capsule type endoscope 2H further includes an emergency power supply 125. When control means 9 determines that the electrical energy stored in the power storage means 124 including, e.g., a large-capacitance capacitor, is low, the control means 9 controls a switch 126 to supply power from the emergency power supply 125 to respective means. The control means 9 is connected to an RF-ID unit 127 or the like. After the capsule type endoscope 2H is excreted from the body, image data stored in the recording means 11 can be transmitted from the RF-ID unit 127 through the control means 9 by RF (radio frequency).

The power feed means 122, arranged on the outside of the body, includes a feed coil or the like. The power receiving means 123 includes a coil, such as a solenoid. In this case, preferably, a high-permeability magnetic material is disposed within the coil to increase the generating efficiency.

The capsule type endoscope 2H is used in the body of a patient. After being excreted from the body, the capsule type endoscope 2H is washed and disinfected. Then, the capsule type endoscope 2H is received in a clean bag 131 as shown in FIG. 19.

When the capsule type endoscope 2H is put on a reader 132, the RF-ID unit 127 transmits image data recorded in the recording means 11 by radio and the reader 132 reads the image data. The image data read by the reader 132 is recorded on extracorporeal recording means 133 and is also transmitted to display control means 134, so that an image is displayed on a display 135.

A method for displaying images on the display 135 can be set in accordance with information input from a display-method input unit 136.

The case of using the RF-ID unit 127 has been described. Illuminating means 5 may be used.

For example, after a predetermined lapse of time, the control means 9 demodulates image data recorded in the recording means 11 and transmits the data using light to the outside of the body through the illuminating means 5. A photoreceptor (not shown) using a photo diode or the like is provided for the reader 132. The transmitted data may be received by the photoreceptor.

According to the present embodiment, the system does not include means for transmitting image data by radio from the inside of the body to the outside through body tissue. Advantageously, an internal examination can be performed without time and trouble.

According to the above-described embodiments, in the use of a plurality of image pickup means for generating different images, the images can be appropriately displayed in such a display mode that a diagnosis can be easily made.

The use of a capsule type endoscope including different kinds of image pickup means can achieve lower image pickup omission than that in the use of an capsule type endoscope including one image pickup means. In addition, different kinds of images lead to the improvement of the capability to facilitate a diagnosis.

Modifications obtained by partially combining the above-described embodiments may be contained in the present invention.

What is claimed is:

1. A capsule type medical system comprising:
   a capsule type endoscope comprising:
      a plurality of image pickup units for generating different image data;
      a storage unit for previously storing image pickup procedures of the plurality of image pickup units; and
      a recording/transmitting unit for recording or transmitting at least a part of different image data captured in accordance with any of the procedures stored in the storage unit in time series, and
   an extracorporeal display unit comprising:
      a display control unit for controlling a method for displaying the different image data recorded or transmitted, wherein the method for displaying can be changed in accordance with information regarding an input of a display method which is inputted to a display-method input unit connected to the display control unit and information regarding a display method different from the image pickup procedures stored in the storage unit of the capsule type endoscope.

2. The capsule type medical system according to claim 1, wherein according to the display method by the display control unit, different image data captured by the capsule type endoscope are simultaneously displayed on a screen of the display unit.

3. The capsule type medical system according to claim 1, wherein according to the display method by the display control unit, different image data captured by the capsule type endoscope are sequentially displayed in time series in the order of image pickup on a screen of the display unit.

4. The capsule type medical system according to claim 1, wherein according to the display method by the display control unit, image data obtained by capturing images of substantially the same portion with different angles through the capsule type endoscope are displayed as a stereoscopic image combined for three-dimensional observation on a screen of the display unit.

5. The capsule type medical system according to claim 1, wherein according to the display method by the display control unit, one of the different image data is displayed as a normal or wide-range observation image, the other image data is displayed as a magnified observation image obtained by partially enlarging an observation range corresponding to the normal or wide-range observation image, and those observation images are simultaneously displayed on a screen of the display unit.

6. The capsule type medical system according to claim 5, wherein the displaying method by the display control unit displays a mark overlapped at a position in the normal or wide-range observation image, the position corresponding to the magnified observation image.

7. The capsule type medical system according to claim 1, wherein according to the display method by the display control unit, one of the different image data is displayed as a normal observation image and the other image data is displayed as a special-light observation image on a screen of the display unit.

8. The capsule type medical system according to claim 7, wherein the special-light observation image is a narrow-band observation image, an infrared observation image, or a fluorescent observation image.

9. The capsule type medical system according to claim 1, wherein the different image data include at least two of image data obtained by forward direct-view or oblique-view image pickup in the lengthwise direction of the capsule, image data obtained by backward direct-view or oblique-view image pickup in the lengthwise direction thereof, and image data obtained by image pickup in one direction or substantially all around directions.

10. The capsule type medical system according to claim 1, wherein the plurality of image pickup units include a common image pickup element.

11. The capsule type medical system according to claim 1, further comprising:
   a rotating driving unit for rotating the capsule type endoscope about the center axis in the lengthwise direction of a capsule body.

12. The capsule type medical system according to claim 1, wherein when the capsule type endoscope records or transmits the image data, information regarding the kind of the capsule type endoscope or the image pickup unit or identification information is added to image data.

13. The capsule type medical system according to claim 12, wherein according to the display method by the display control unit, different images are displayed in accordance with the respective information regarding the kind or the identification information.

14. The capsule type medical system according to claim 13, wherein the displaying method by the display control unit displays respective images corresponding to the different images in accordance with the information regarding the kind or the identification information, and displays information based on the information regarding the kind and/or the identification information adjacent to the respective images.

15. The capsule type medical system according to claim 1, wherein the displaying method by the display control unit displays, on a screen of the display unit, a stereoscopic image combined for three-dimensional observation and a two-dimensional image from which the stereoscopic image is generated.

* * * * *